(12) United States Patent
Gravel et al.

(10) Patent No.: US 10,416,146 B2
(45) Date of Patent: Sep. 17, 2019

(54) ROTARY TIMBER CHARGER WITH STIFFNESS MEASURING MECHANISM

(71) Applicant: VAB MACHINES INC., Lévis (CA)

(72) Inventors: Claude Gravel, St-Ferréol les Neiges (CA); David Larochelle, St-Marc-de-Figuery (CA)

(73) Assignee: VAB MACHINES INC., Levis, Quebec (CA)

( * ) Notice: Subject to any disclaimer, the term of this patent is extended or adjusted under 35 U.S.C. 154(b) by 835 days.

(21) Appl. No.: 14/918,060

(22) Filed: Oct. 20, 2015

(65) Prior Publication Data

US 2016/0109427 A1    Apr. 21, 2016

Related U.S. Application Data

(60) Provisional application No. 62/065,875, filed on Oct. 20, 2014.

(51) Int. Cl.
   *G01N 3/20*    (2006.01)
   *G01N 33/46*   (2006.01)
   *B27B 25/00*   (2006.01)

(52) U.S. Cl.
   CPC ............. *G01N 33/46* (2013.01); *B27B 25/00* (2013.01)

(58) Field of Classification Search
   CPC .......... G01N 33/46; G01N 3/20; B27B 25/00; B65G 47/847; B23Q 7/001
   See application file for complete search history.

(56) References Cited

FOREIGN PATENT DOCUMENTS

| CA | 2151768 A1 | 12/1996 | |
|---|---|---|---|
| CA | 2185609 A1 | 12/1996 | |
| CA | 2363092 A1 | 5/2001 | |
| WO | WO 01/38849 | * 5/2001 | ............... G01N 3/20 |

* cited by examiner

*Primary Examiner* — Harshad R Patel
*Assistant Examiner* — Nigel H Plumb
(74) *Attorney, Agent, or Firm* — Eversheds Sutherland (US) LLP (57) ABSTRACT

A rotary timber charger including a charging assembly and a stiffness measuring mechanism. The charging assembly includes a continuously rotating main rotatable shaft with at least two transfer wheels mounted thereto and each having a timber piece grasping assembly grasping, retaining and releasing a piece of timber continuously moved between a grasping position and a release position. The stiffness measuring mechanism includes a load application wheel positioned between consecutive transfer wheels and momentarily applying a load on the piece of timber during rotation of the piece of timber between the grasping position and the release position and a deformation measuring system measuring a deformation of the transferred piece of timber following the application of the load thereon.

9 Claims, 9 Drawing Sheets

ROTARY TIMBER CHARGER WITH STIFFNESS MEASURING MECHANISM

CROSS REFERENCE TO RELATED APPLICATION

This application claims the benefit under 35 U.S.C. § 119(e) of U.S. provisional patent application No. 62/065,875 which was filed on Oct. 20, 2014. The entirety of the aforementioned application is herein incorporated by reference.

TECHNICAL FIELD OF THE INVENTION

The present invention relates to the field of timber stiffness measurement and timber grading. More particularly, it relates to a mechanism for measuring the stiffness of a piece of timber, a rotary timber charger including a mechanism for measuring the stiffness of a piece of timber and a method of operation for same.

BACKGROUND

It is known in the art to measure the stiffness of timber pieces in order to perform non-destructive stress grading thereof based on the measured stiffness and correlated strength of each one of the timber pieces.

Known methods to measure the stiffness of timber pieces commonly include taking a number of measurements of stiffness over a length of a piece of timber (for example, on its side in the case of a plank). In order to perform such measurements, each one of the pieces of timber can be moved either longitudinally or transversally, with supports for supporting a section of the piece of timber in place and a load to apply a force on another section of the piece of timber, between the supports.

Canadian patent application no. 2,363,092 discloses an apparatus for grading timber pieces, where measuring of the stiffness of each piece of timber is performed by applying a force to the piece of timber, at a point intermediate its length, as the piece of timber is supported at or near the ends thereof, without moving the piece of timber lengthwise. In order to measure the stiffness of the piece of timber, the patent application describes that either a predetermined force can be applied by a ram and the resulting deflection of the piece of timber measured, or the force required to deflect the piece of timber by a predetermined amount can be measured. The document discloses that a single measurement can be taken by, for example, applying a force and measuring the resulting deflection of the piece of timber, or two or more measurements can be taken by applying a first predetermined force and measuring the resulting deflection and subsequently applying, for example, a second higher force and measuring the resulting deflection.

The above described methods and apparatuses to grade pieces of timber using measurement of a stiffness thereof however suffer from several drawbacks. Indeed, in order to measure the stiffness of the timber pieces using such methods and apparatuses, a dedicated machine must be added to the production line, which requires additional space and increases the time required for a piece of timber to travel along the production line. Moreover, given that pieces of timber are not all identical, the measurements obtained for a piece of timber can be biased by the natural curvature of the piece of timber and/or by imperfections (tears, holes, slits or the like) on the surface from which the measurements are taken.

In view of the above, there is a need for an improved mechanism for measuring the stiffness of a piece of timber which would be able to overcome or at least minimize some of the above-discussed prior art concerns.

BRIEF SUMMARY OF THE INVENTION

According to a first general aspect, there is provided a rotary timber charger. The rotary timber charger comprises a charging assembly with at least two transfer wheels spaced apart from one another and mounted to a main rotatable shaft, each one of the at least two transfer wheels having at least one timber piece grasping assembly operative to grasp a section of a piece of timber at a grasping position, release the section of the piece of timber at a release position, and retain the section of the piece of timber between the grasping position and the release position. The rotary timber charger also comprises a stiffness measuring mechanism with at least one load application wheel positioned between consecutive transfer wheels, each one of the at least one load application wheel comprising at least one load application member configured to momentarily apply a load on the piece of timber retained by a corresponding one of the at least one timber piece grasping assembly of the consecutive ones of the at least two transfer wheels. The stiffness measuring mechanism also comprises a deformation measuring system with at least one surface position measuring assembly measuring a first position of a measure surface of the piece of timber and a second position of the measure surface of the piece of timber, the second position of the measure surface being angularly spaced-apart from the first position, with the load being applied by the at least one load application member of the at least one load application wheel in at least one of the first position and the second position of the measure surface.

In an embodiment, the main rotatable shaft of the charging assembly rotates continuously.

In an embodiment, the first position of the measure surface is an angular position thereof without the load being applied by the load application member of the at least one load application wheel.

In an embodiment, the at least one load application wheel is mounted to the main rotatable shaft and rotates simultaneously with the at least two transfer wheels.

In an embodiment, each one of the at least one load application member of the at least one load application wheel includes a load application rod mounted to the load application wheel and a translation actuator operatively connected thereto to translate the load application rod between an inactive configuration wherein a timber piece abutting end of the load application rod is spaced apart from a contact surface of the piece of timber, opposed to the measured surface, and an active configuration wherein the timber piece abutting end of the load application rod abuts the contact surface of the piece of timber.

In an embodiment, the at least one load application wheel comprises a plurality of load application members and each one of the at least two transfer wheels comprises a plurality of grasping assemblies, the amount of load application members corresponding to the amount of grasping assemblies and each one of the plurality of load application members being angularly aligned with a corresponding one of the plurality of grasping assemblies.

In an embodiment, the rotary timber charger further comprises a rotary encoder indicating an angular position of the main rotatable shaft and the at least one surface position measuring assembly of the deformation measuring system is calibrated using the rotary encoder.

In an embodiment, the at least one surface position measuring assembly of the deformation measuring system includes a first surface position measuring assembly configured to measure one of the position of the measure surface of the piece of timber without the load being applied by the load application member of the at least one load application wheel and the position of the measure surface of the piece of timber with the load being applied by the load application member of the at least one load application wheel and a second surface position measuring assembly configured to measure the other one of the position of the measure surface of the piece of timber without the load being applied by the at least one load application member of the load application wheel and the position of the measure surface of the piece of timber with the load being applied by the load application member of the at least one load application wheel.

In an embodiment, each one of the at least one timber piece grasping assembly comprises a first and a second grasping members cooperating to engage opposite surfaces of the piece of timber and the load application member is mounted peripherally to a respective one of the at least one load application wheel and extends substantially tangentially thereto.

According to another general aspect, there is also provided, a stiffness measuring mechanism for a rotary timber charger having a rotatable charging assembly including at least one set of timber piece grasping assemblies and being operative to transfer successive pieces of timber from a first carrier assembly to a second carrier assembly. The stiffness measuring mechanism comprises at least one load application wheel positioned between consecutive grasping assemblies of the at least one set of timber grasping assemblies of the rotatable charging assembly, the at least one load application wheel comprising at least one load application member configurable between an inactive configuration where no load is applied on a transferred piece of timber and an active configuration where a load is applied on the transferred piece of timber. The stiffness measuring mechanism also comprises a deformation measuring system comprising at least one surface position measuring assembly measuring a first position of a measure surface of the transferred piece of timber and a second position of the measure surface of the transferred piece of timber. The stiffness measuring mechanism operates concurrently with the rotatable charging assembly transferring the successive pieces of timber from the first carrier assembly to the second carrier assembly.

In an embodiment, the first position of the measure surface of the transferred piece of timber corresponds to the inactive configuration of a corresponding one of the at least one load application member and the second position of the measure surface of the transferred piece of timber corresponds to the active configuration of the corresponding one of the at least one load application member.

In an embodiment, the charging assembly of the rotary timber charger comprises a main shaft rotatable to engage in rotation the at least one set of timber piece grasping assemblies and the at least one load application wheel.

In an embodiment, the stiffness measuring mechanism further comprises a rotary encoder indicating an angular position of the main rotatable shaft and the at least one surface position measuring assembly of the deformation measuring system is calibrated using the rotary encoder.

In an embodiment, each one of the at least one load application member of the at least one load application wheel includes a load application rod mounted to the load application wheel and a translation actuator operatively connected thereto to translate the load application rod between the inactive configuration wherein a timber piece abutting end of the load application rod is spaced apart from a contact surface of the piece of timber, opposed to the measured surface, and the active configuration wherein the timber piece abutting end of the load application rod abuts the contact surface of the piece of timber.

In an embodiment, the at least one load application wheel comprises a plurality of load application members and the rotatable charging assembly comprises at least two transfer wheels, wherein each one of the at least two transfer wheels comprises a plurality of grasping assemblies, the amount of load application members corresponding to the amount of grasping assemblies and each one of the plurality of load application members being angularly aligned with a corresponding one of the plurality of grasping assemblies.

According to another general aspect, there is also provided a method for measuring a stiffness of successive pieces of timber, for each one of the successive pieces of timber. The method comprises the steps of: grasping the piece of timber at a grasping position; rotating the piece of timber towards a release position; and releasing the piece of timber. Concurrently with the step of rotating the piece of timber towards the release position, the method further comprises measuring a position of a measure surface of the piece of timber at a first measurement position; applying a load on the piece of timber; measuring a position of the measure surface of the piece of timber at a second measurement position as the load is applied on the piece of timber; and removing the load from the piece of timber.

In an embodiment, the step of rotating the piece of timber towards the release position is performed by a continuous rotation of the piece of timber.

In an embodiment, the first measurement position is the position of the measure surface of the piece of timber without the load being applied on the piece of timber.

In an embodiment, the step of grasping the piece of timber at a grasping position and continuously rotating the piece of timber towards a release position comprise temporarily engaging opposite surfaces of the piece of timber at grasping positions along a length of the piece of timber.

In an embodiment, the step of applying a load on the piece of timber comprises engaging the piece of timber using at least one load application member, along at least one section of the piece of timber located between the grasping positions.

BRIEF DESCRIPTION OF THE DRAWINGS

Other objects, advantages and features will become more apparent upon reading the following non-restrictive description of embodiments thereof, given for the purpose of exemplification only, with reference to the accompanying drawings in which.

DETAILED DESCRIPTION

In the following description, the same numerical references refer to similar elements. The embodiments, geometrical configurations, materials mentioned and/or dimensions shown in the figures or described in the present description are embodiments only, given solely for exemplification purposes.

Moreover, although the embodiments of a stiffness measuring mechanism and rotary timber charger including the stiffness measuring mechanism and corresponding parts thereof consist of certain geometrical configurations as explained and illustrated herein, not all of these components and geometries are essential and thus should not be taken in their restrictive sense. It is to be understood, as also apparent to a person skilled in the art, that other suitable components and cooperation thereinbetween, as well as other suitable geometrical configurations, can be used for the stiffness measuring mechanism and rotary timber charger including the stiffness measuring mechanism, as will be briefly explained herein and as can be easily inferred herefrom by a person skilled in the art. Moreover, it will be appreciated that positional descriptions such as "above", "below", "left", "right" and the like should, unless otherwise indicated, be taken in the context of the figures and should not be considered limiting.

Figure 1:
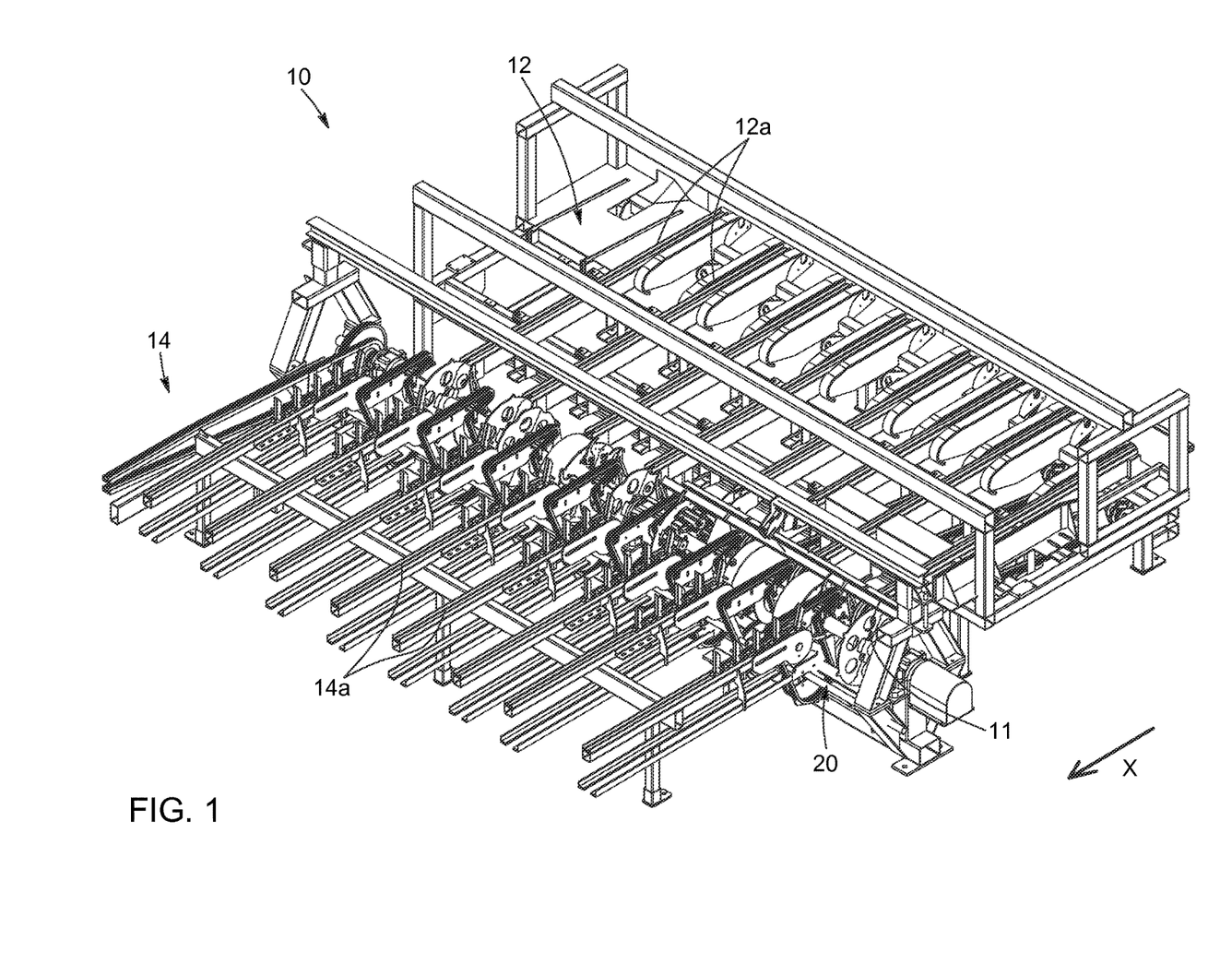
FIG. 1 is a top perspective view of a rotary timber charger with a stiffness measuring mechanism, according to an embodiment.

Referring generally to FIG. 1, in accordance with one embodiment, there is provided a rotary timber charger 10. The rotary timber charger 10 includes a first carrier assembly 12 operative to convey successive pieces of timber 11 (only one piece of timber 11 is shown in FIG. 1), such as without being limitative, wood planks, boards or the like, towards a rotatable charging assembly 20 and a second carrier assembly 14 operative to subsequently convey the pieces of timber 11 away from the rotatable charging assembly 20. Thus, the rotatable charging assembly 20 is mounted between the first carrier assembly 12 and the second carrier assembly 14. In the embodiment shown, the first carrier assembly 12 and the second carrier assembly 14 include a plurality of spaced apart and substantially parallel conveyor chains 12a, 14a to convey the pieces of timber 11 transversally. One skilled in the art would however understand that, in alternative embodiments, the first carrier assembly 12 and/or the second carrier assembly 14 can be embodied by any other conveyor arrangement which allow the pieces of timber 11 to be conveyed transversally to and from the rotatable charging assembly 20.

In view of the above, one skilled in the art will understand that the rotary timber charger 10 can be part of a production line (not shown) which extends along a longitudinal axis X thereof, substantially perpendicular to the length of the pieces of timber 1, with the pieces of timber 11 being transversally conveyed along the longitudinal axis X of the production line. Hence, it will be understood that the pieces of timber 11 are conveyed along the longitudinal axis X of the production line as they are conveyed along the first and second carrier assemblies 12, 14 and the rotatable charging assembly 20 of the rotary timber charger 10.

Figure 2:
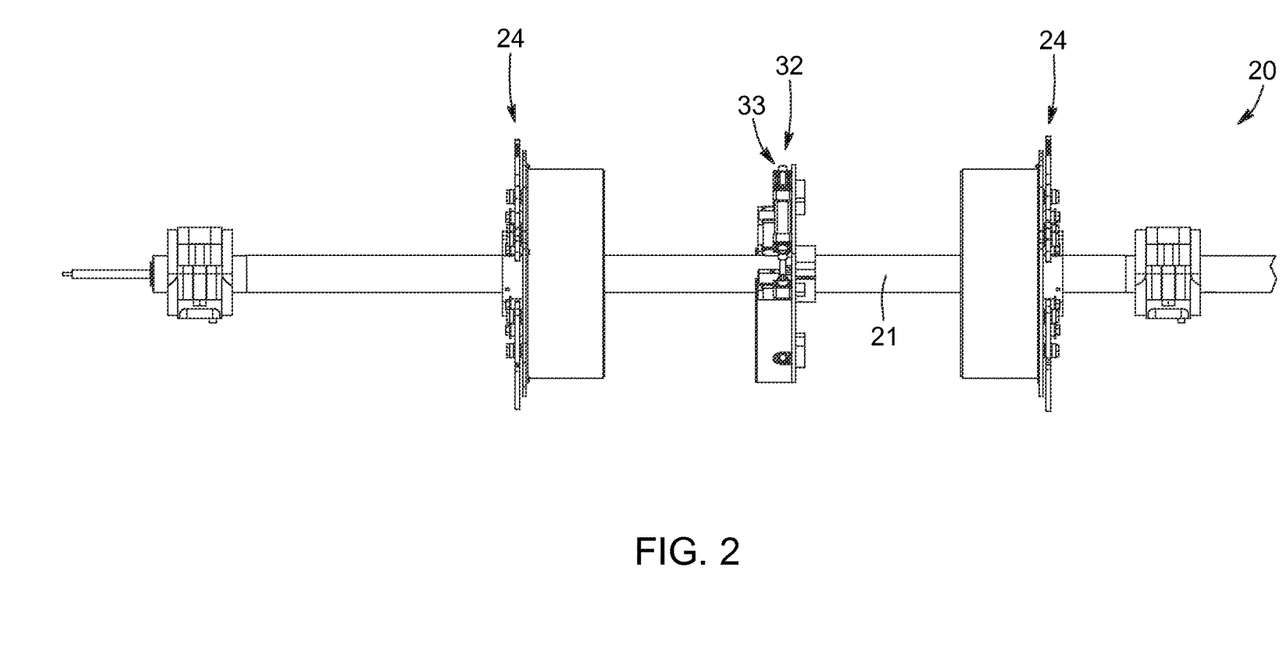
FIG. 2 is a front elevation view, enlarged, of a rotatable charging assembly of the rotary timber charger including the stiffness measuring mechanism of FIG. 1.
Figure 4A:
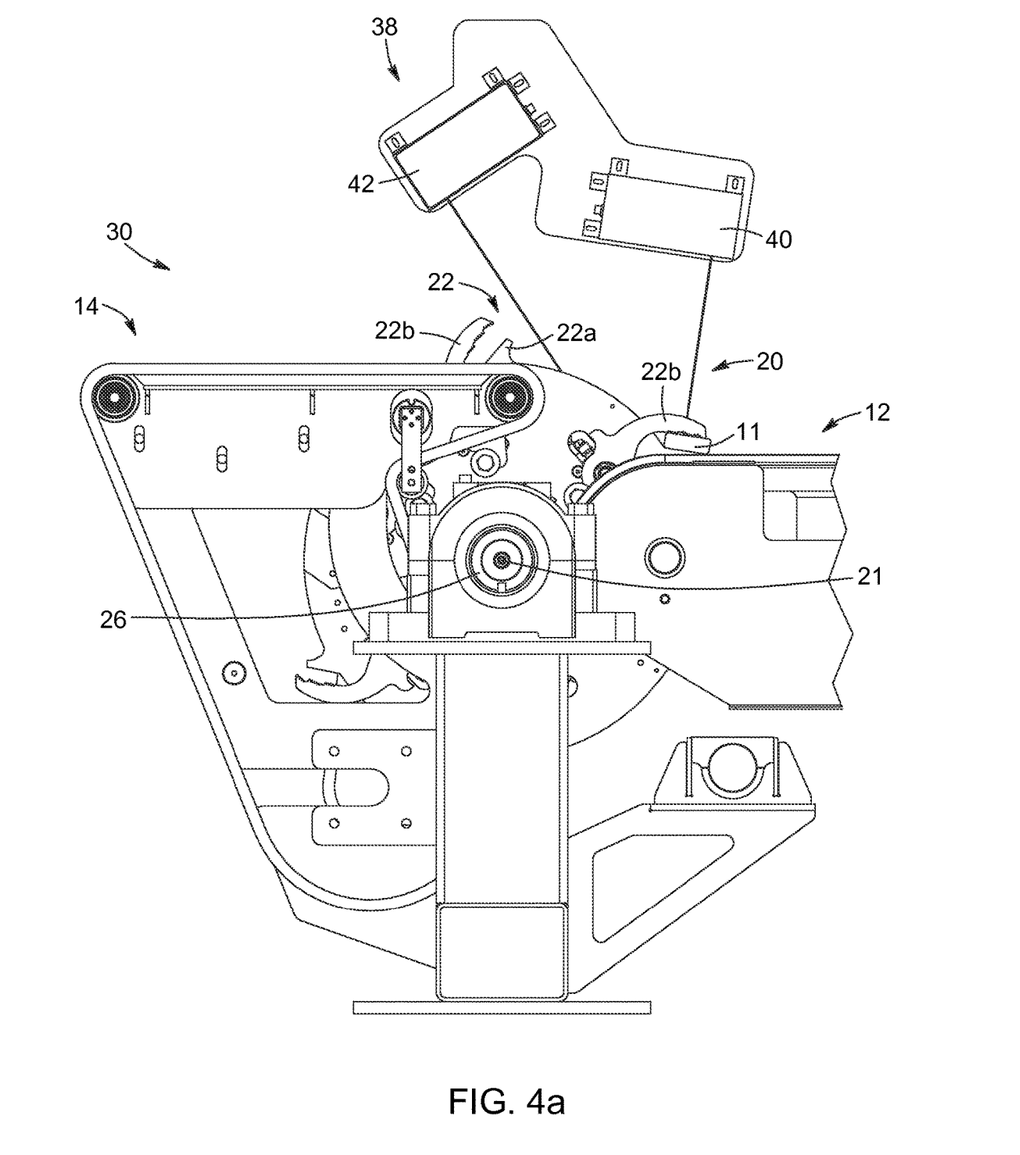
FIG. 4a is a cross-sectional side view of the rotary timber charger including the stiffness measuring mechanism of FIG. 1, showing a piece of timber being grasped by the rotatable charging assembly.

As mentioned above, the rotatable charging assembly 20 transfers the pieces of timber 11 from the first carrier assembly 12 to the second carrier assembly 14. In order to perform such transfer, as shown in FIG. 2, the rotatable charging assembly 20 includes at least two transfer wheels 24 spaced apart from one another and mounted to a main rotatable shaft 21. In an embodiment, the main rotatable shaft 21 continuously rotates about its rotation axis. Referring now to FIG. 4a, there is shown that each one of the transfer wheels 24 includes at least one timber piece grasping assembly 22 operative to grasp a section of a transferred piece of timber 11, at a grasping position, temporarily retain the section of the transferred piece of timber 11 during a rotation of the transfer wheel 24 towards a release position (the piece of timber 11 consequently also being rotated), and subsequently release the transferred piece of timber 11 at the release position. In the embodiment shown, each timber piece grasping assembly 22 includes a first grasping member 22a and a second grasping member 22b which cooperate to temporarily engage opposite surfaces of the transferred piece of timber 11 to perform the grasping, temporary retention and subsequent release of the section of the piece of timber 11 required for transfer thereof. In an embodiment, the first grasping member 22a and second grasping member 22b continuously retain the pieces of timber during the temporary retention.

In an embodiment, the transfer wheels 24 carry the transferred piece of timber 11 between the grasping position and the release position along at least 90° and less than about 270° and, in a particular embodiment, less than about 180°.

One skilled in the art will understand that each one of the at least two transfer wheels 24 has the same amount of grasping assemblies 22, such as to define sets of corresponding grasping assemblies 22 angularly aligned with one another along the at least two transfer wheels 24. Hence, in operation, each set of corresponding grasping assemblies 22 of the at least two transfer wheels 24, grasp, maintain and release the transferred pieces of timber 11 simultaneously.

In the embodiment shown, each one of the transfer wheels 24 includes a plurality of angularly spaced-apart timber piece grasping assembly 22, each one including a first grasping member 22a and a second grasping member 22b.

In the embodiment shown, two transfer wheels 24 are provided. Each one of the transfer wheels 24 is positioned for an associated timber piece grasping assembly 22 to grasp a section of the transferred piece of timber 11 close to an end thereof, during the transfer from the grasping position (on the first carrier assembly 12) to the release position (on the second carrier assembly 14). One skilled in the art will understand that, in an alternative embodiment, more than two transfer wheels 24 can be provided along a width of the rotatable charging assembly 20, such that grasping assemblies 22 of terminal transfer wheels 24 (i.e. transfer wheels 24 positioned at the ends of the rotatable charging assembly 20) can grasp a section of the transferred pieces of timber 11 proximate to an end thereof and grasping assemblies 22 of intermediate transfer wheels 24 (i.e. transfer wheels 24 other than the terminal transfer wheels 24) engage a section of the transferred pieces of timber 11 between the terminal transfer wheels 24.

In order to measure a stiffness of each one of the pieces of timber 11 being transferred by the rotatable charging assembly 20, the rotatable charging assembly 20 also includes a stiffness measuring mechanism 30.

Figure 3:
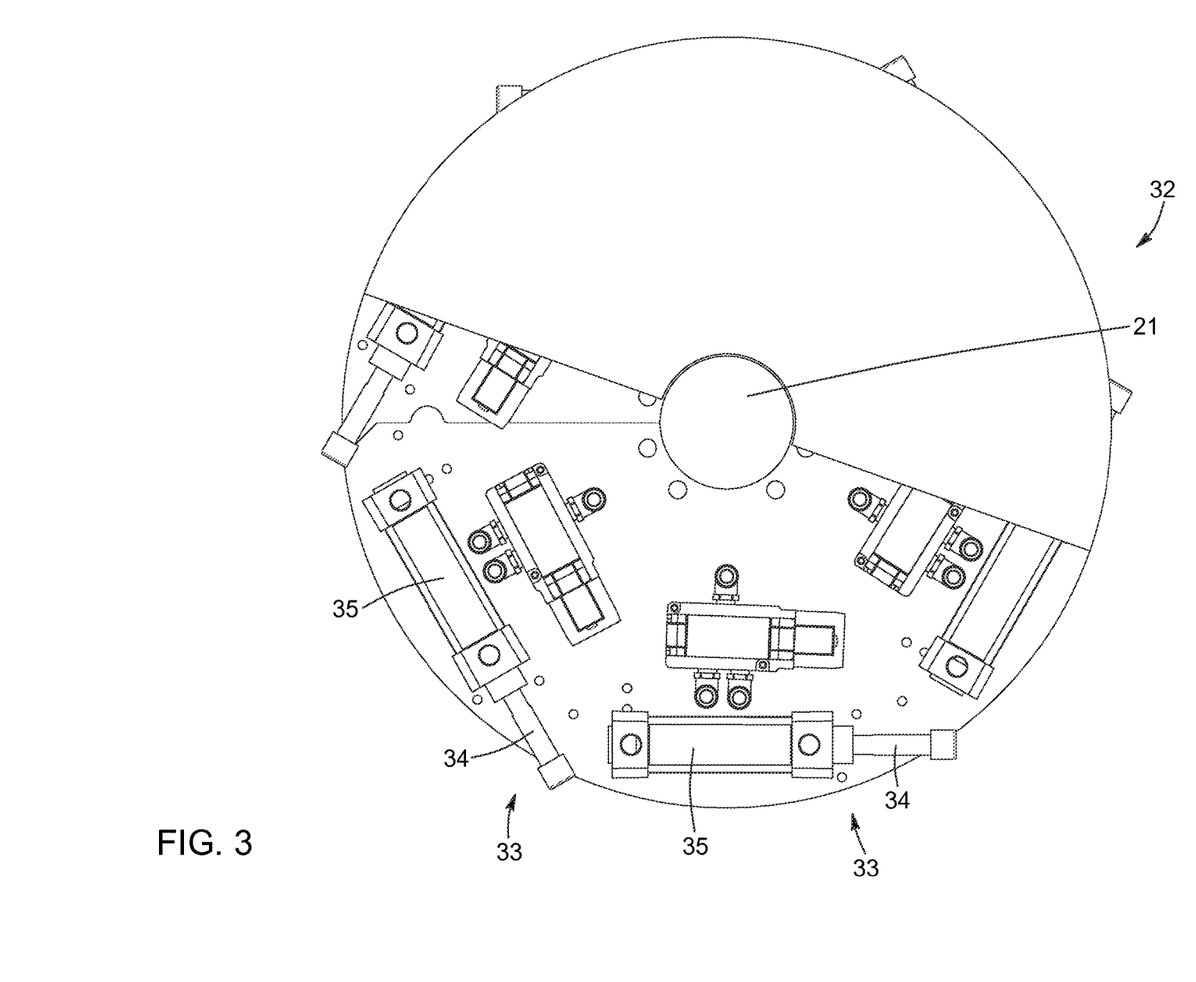
FIG. 3 is a side elevation view, enlarged, of a load application wheel of the rotary timber charger including the stiffness measuring mechanism of FIG. 1, shown with a cover partially removed.

Referring now to FIGS. 2 and 3, there is shown that, in the embodiment shown, the stiffness measuring mechanism 30 includes at least one load application wheel 32, with at least one load application member 33, operative to apply a momentary load (or force) on a transferred piece of timber 11, as it is being transferred by the rotatable charging assembly 20 from the first carrier assembly 12 to the second carrier assembly 14. For example and without being limitative, in an embodiment, the momentary load can be applied during a range of between about 50 milliseconds and about 150 milliseconds. Referring to FIG. 4a, there is shown that the stiffness measuring mechanism 30 also includes a deformation measuring system 38 operative to determine the deformation of the transferred piece of timber 11 upon application of the load thereon, based on measures of the transferred piece of timber 11. Each load application wheel 32 is mounted to the main rotatable shaft 21, between consecutive ones of the transfer wheels 24. Therefore, it will be understood that, in an embodiment (not shown) where more than two transfer wheels 24 are mounted to the main rotatable shaft 21, multiple load application wheels 32 can be mounted to the main rotatable shaft 21, each one of the multiple load application wheel 32 being positioned between consecutive ones of the transfer wheels 24.

In the embodiment shown, a single load application wheel 32 is mounted to the main rotatable shaft 21 and is centered between the corresponding transfer wheels 24. One skilled in the art will understand that, in an alternative embodiment, the load application wheel 32 could be off-center relative to the adjacent ones of the transfer wheels 24. Moreover, one skilled in the art will understand that, in another alternative embodiment, more than one load application wheel 32 can be mounted to the main rotatable shaft 21, between adjacent ones of the transfer wheels 24.

Referring to FIG. 3, in the embodiment shown, each load application member 33 includes a load application rod 34 peripherally mounted to the load application wheel 32 and extending substantially tangentially thereto. Each load application member 33 also includes a translation actuator 35 operatively connected to a respective one of the load application rod 34. Each translation actuator 35 is operative to momentarily drive the load application rod 34 longitudinally, to move the load application rod 34 towards the transferred piece of timber 11. More particularly, the translation actuator 35 is operative to momentarily drive the load application rod 34 in a manner such that a timber piece abutting end thereof extends outward of a peripheral edge of the load application wheel 32. The outward movement of the load application rod 34 results in the load application rod 34 contacting a contact surface 11a of the timber element 11, thereby applying a force on the transferred piece of timber 11 during a momentary time period. The translation actuator 35 also operates to subsequently retract the load application rod 34 to remove the force applied on the contact surface 11a of the transferred piece of timber 11. Thus, the load application rod 34 translates between an inactive configuration wherein it is spaced apart from the contact surface 11a of the transferred piece of timber 11 and an active configuration wherein its timber piece abutting end abuts the contact surface 11a of the transferred piece of timber 11 maintained by the timber piece grasping assembly 22 of the transfer wheels 24. In an embodiment, in the inactive configuration, the load application rod 34, including the timber piece abutting end, is entirely located inside the periphery (i.e. inside the peripheral edge) of the load application wheel 32.

In an embodiment, the amount of load application rods 34 of each load application wheel 32 is similar to the amount of sets of grasping assemblies 22 of the transfer wheels 24, such that each one of the load application rods 34 is associated with one of the sets of grasping assemblies 22 of the transfer wheels 24. As will be easily understood by one skilled in the art, given that, in the embodiment shown, each load application wheel 32 and transfer wheels 24 are mounted to a common main rotatable shaft 21, the load application wheel 32 and transfer wheels 24 rotate at a similar frequency of rotation (rpm) and remain in the same angular position relative to one another throughout operation of the rotary timber charger 10.

In an embodiment, the rotatable charging assembly 20 includes an electronic control system operatively connected to the grasping assemblies 22 of the transfer wheels 24 and the translation actuators 35 operatively connected to the load application rods 34 such that the operation of each set of grasping assemblies 22 for grasping, maintaining and releasing the transferred piece of timber 11 being transferred, is synchronized with the movement of the load application rods 34, actuated by the translation actuators 35. Hence, the force is applied on the transferred piece of timber 11, as sections of the transferred piece of timber 11 are being maintained and supported by the set of grasping assemblies 22. The operation of the combination of each set of grasping assemblies 22 and the corresponding load application rod 34 will be explained in more details below.

In the embodiment shown, the translation actuator 35 is a pneumatic cylinder, but one skilled in the art will understand that, in alternative embodiments, the translation actuator can be any mechanism which drives the load application rod 34 longitudinally (i.e. any linear actuator), such as, without being limitative, a hydraulic cylinder, an electric cylinder or the like. In an embodiment, the translation actuator 35 can be a servomotor.

One skilled in the art will also understand that, in other alternative embodiments, the load application member 33 could differ from the plurality of load application rod and translation actuator assemblies of the embodiment shown and any other load application mechanism which can apply a momentary load on the piece of timber 11 can be used. For example and without being limitative, in an embodiment (not shown), the load application member 33 could rather include a clamping assembly, with the load application wheel 32 being connected to a rotatable actuation mechanism. The clamping assembly can be displaceable between the inactive configuration (where no load is applied on the transferred timber piece) and the active configuration (where a load is applied on the transferred timber piece) by the action of the rotatable actuation mechanism connected to the load application wheel 32, such as to clamp a section of the transferred piece of timber 11 and apply or release the force on the transferred piece of timber 11 by rotation, as sections of the transferred piece of timber 11 are being maintained and supported by the set of grasping assemblies 22. In such an embodiment, the rotatable actuation mechanism can be any rotary actuator, such as an electric actuator connected to a secondary rotatable shaft different from the above mentioned main rotatable shaft 21, onto which the load application wheel 32 is mounted and driving the secondary rotatable shaft in rotation. In an embodiment, the rotatable actuation mechanism can be a servomotor. One skilled in the art will understand that, in an embodiment, a plurality of clamping assemblies could also be provided, each one of the clamping assembly corresponding to a set of grasping assemblies 22.

Figure 4B:
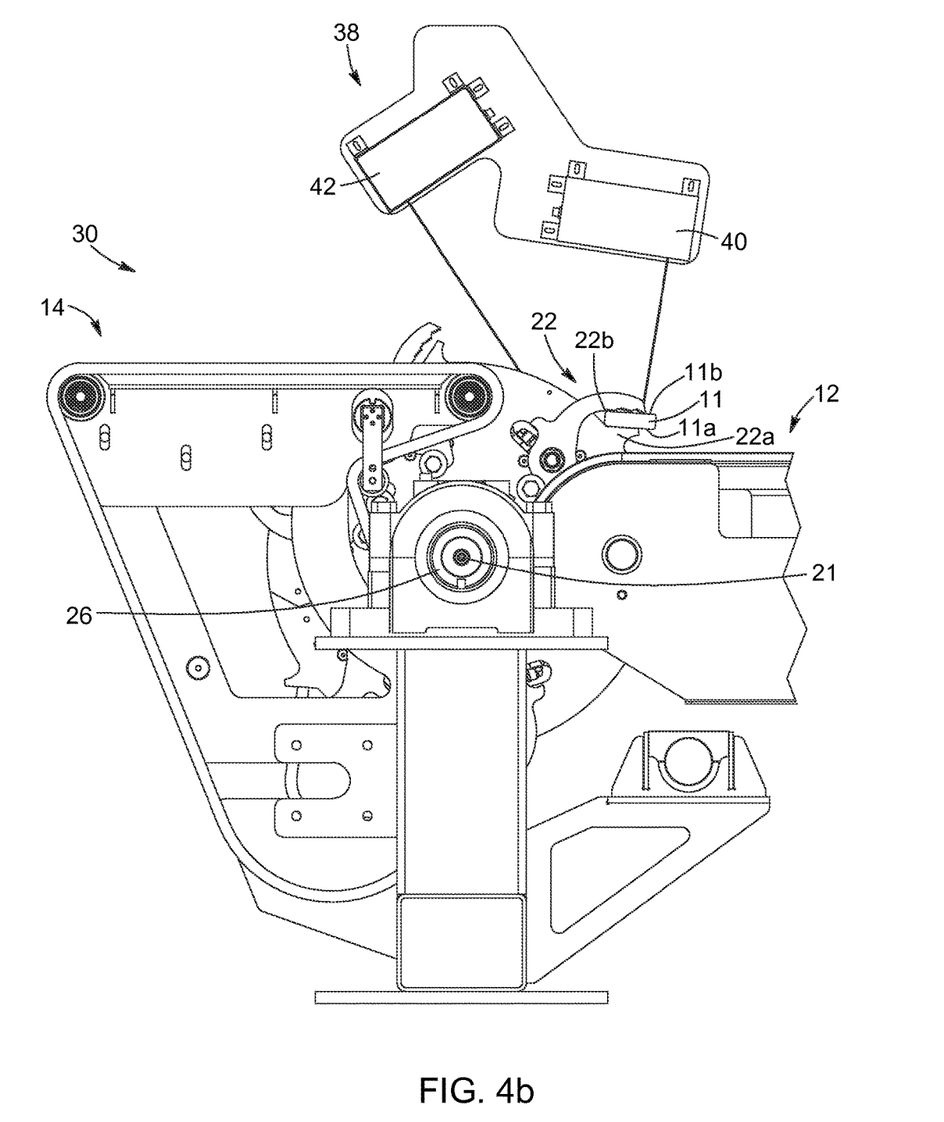
FIG. 4b is a cross-sectional side view of the rotary timber charger including the stiffness measuring mechanism of FIG. 1, showing an initial measurement of a position of a measure surface of the piece of timber grasped by the rotatable charging assembly.
Figure 4C:
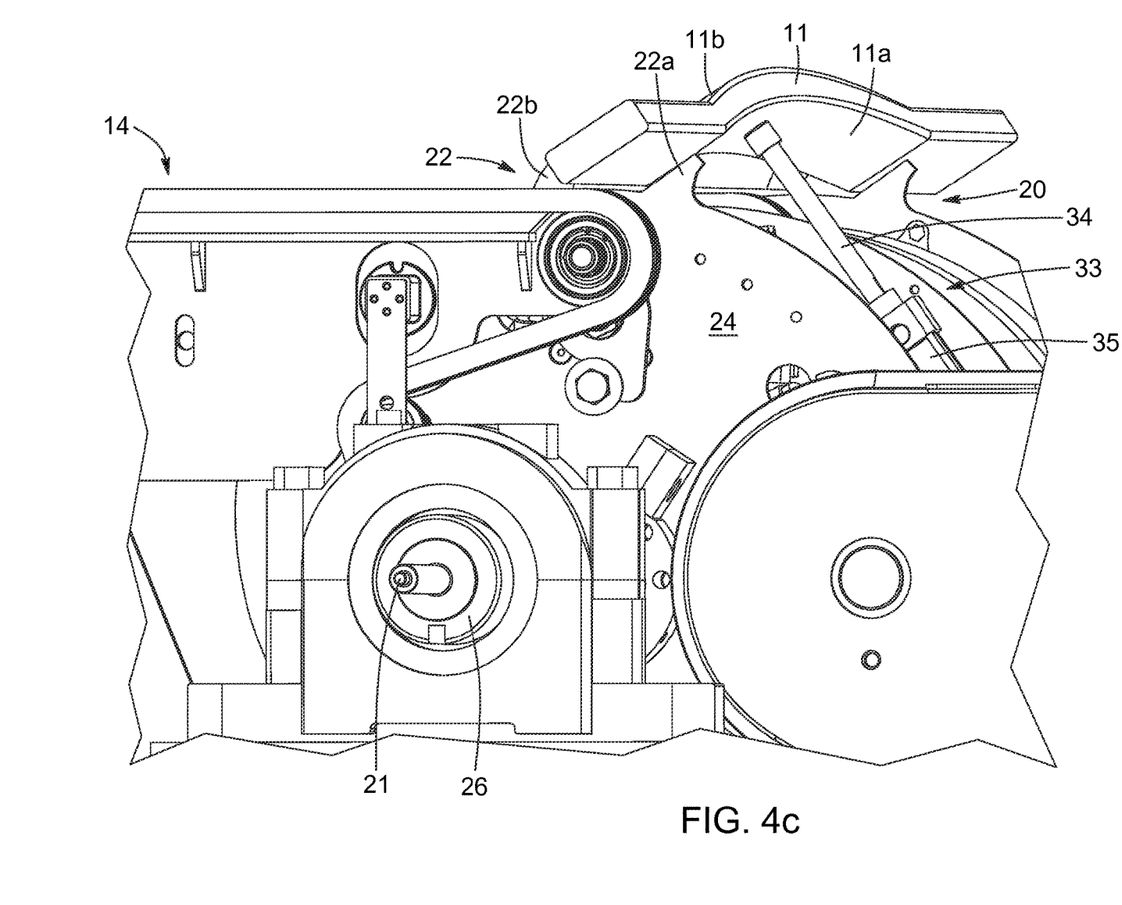
FIGS. 4c and 4d are respectively a perspective view, enlarged, and a cross-sectional side view of the rotary timber charger including the stiffness measuring mechanism of FIG. 1, showing a force being applied on the piece of timber by a load application rod of the load application wheel and a simultaneous measurement of a position of the measure surface of the piece of timber.
Figure 4D:
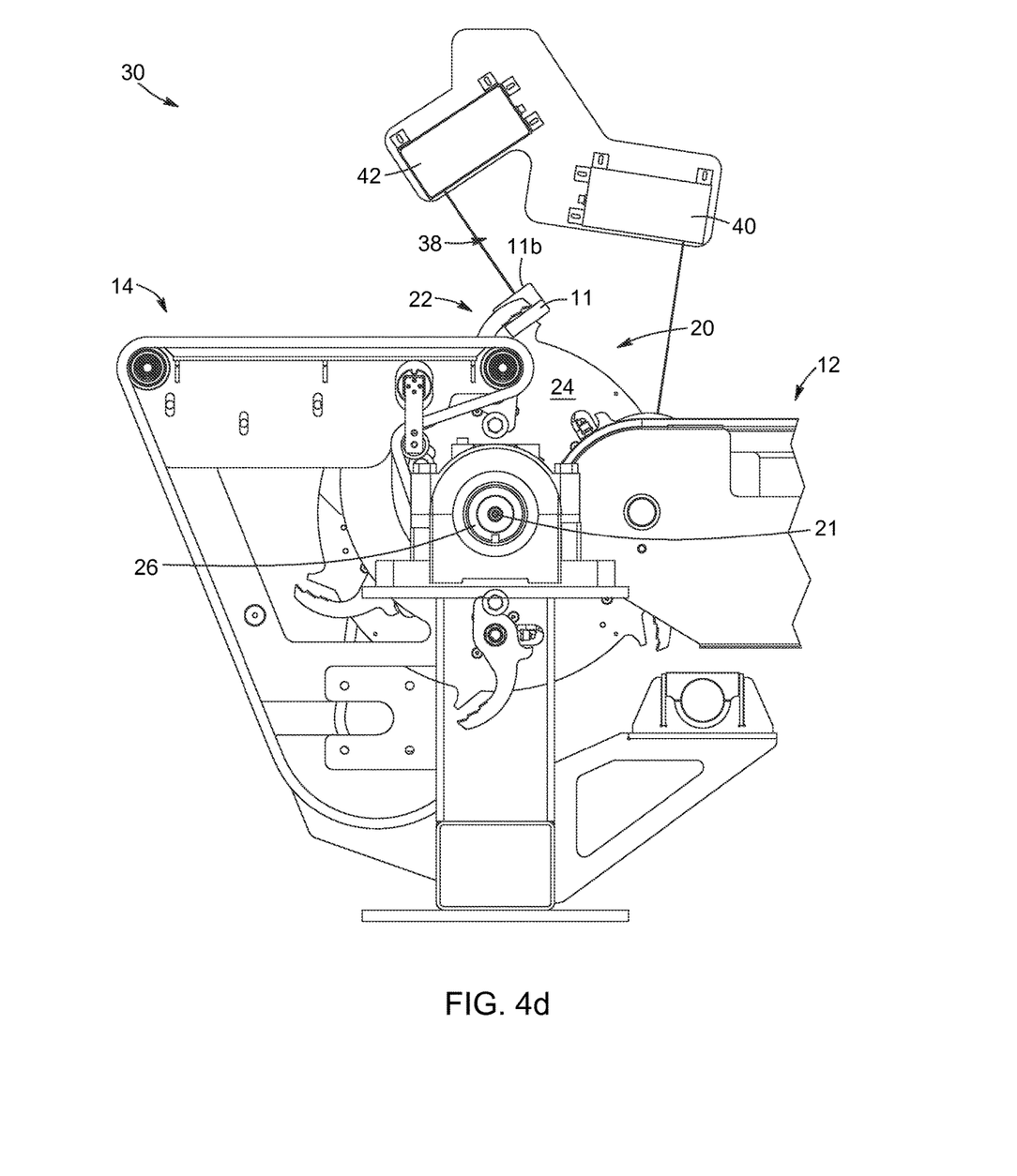

In the embodiment shown, referring to FIGS. 4*a* and 4*b*, the deformation measuring system 38 of the stiffness measuring mechanism 30 determines the deformation of the transferred piece of timber 11 using a first surface position measuring assembly 40 and a second surface position measuring assembly 42. The first surface position measuring assembly 40 measures the position of a measure surface 11*b* of the transferred piece of timber 11 at a first measurement position, before the application of the force thereon by a corresponding one of the load application members 33, and the second surface position measuring assembly 42 measures the position of the measure surface 11*b* of the transferred piece of timber 11, at a second measurement position, with the force being applied on the contact surface 11*a* of the transferred piece of timber 11 by the load application member 33. One skilled in the art will understand that the first measurement position and the second measurement position are angular position of the transferred piece of timber 11, angularly spaced apart from one another, as the transferred piece of timber 11 is being transferred by the rotatable charging assembly 20.

In an embodiment, in order to allow the continuous and uninterrupted operation of the rotary timber charger 10, i.e. continuous rotation, the load application member 33 applies the force on the transferred piece of timber 11 and the deformation measuring system 38 measures the position of the measure surface 11*b* of the transferred piece of timber 11 concurrently as the rotatable charging assembly 20 transfers it from the first carrier assembly 12 to the second carrier assembly 14. Hence, the stiffness measuring mechanism 30 does not interfere or negatively impact on the operation of the rotatable charging assembly 20, the main rotatable shaft 21 of the rotatable charging assembly 20 rotating continuously to transfer the corresponding piece of timber 11 from the first carrier assembly 12 to the second carrier assembly 14.

One skilled in the art will understand that in the course of the present application, the expressions "without the force/load being applied on the transferred piece of timber" before the force/load being applied on the transferred piece of timber" or any corresponding expressions are understood to also include instances where a minimal load, for example and without being limitative, a load of less than about three pounds, is being applied on the transferred piece of timber 11.

One skilled in the art will understand that, in an embodiment, the deformation measuring system 38 is configured to measure the position of the measure surface 11*b* of the transferred piece of timber 11 of the transferred piece of timber 11 at different points along the length of the transferred piece of timber 11, i.e. between each one of the transfer wheels 24 of the rotatable charging assembly 20 where the transferred piece of timber 11 is caused to deform by the momentary application of a force by the load application member 33. Hence it will be understood that, in an embodiment, each one of the first surface position measuring assembly 40 and the second surface position measuring assembly 42 can include multiple sub-assemblies, each configured to measure the position of the measure surface 11*b* of the transferred piece of timber 11 at one of the different points along the length of the transferred piece of timber 11.

Once the position of the surface of the transferred piece of timber 11, with and without the force being applied to the transferred piece of timber 11, has been gathered by the first surface position measuring assembly 40 and the second surface position measuring assembly 42, one skilled in the art will understand that the deformation of the transferred piece of timber 11 can easily be determined by calculations, for example and without being limitative, by a processor (not shown) coupled to the rotatable charging assembly 20, stiffness measuring mechanism 30 and deformation measuring system 38. One skilled in the art will understand that from the calculated deformation of the transferred piece of timber 11 and specific additional known data such as, without being limitative, the force applied by the load application member 33, the longitudinal position of the load application member 33 with regards to the transferred piece of timber 11, the span between the grasping assemblies 22, the thickness of the transferred piece of timber 11, or the like, the stiffness of the transferred piece of timber 11 can be calculated by the processor (for example by calculating the Young's modulus of the transferred piece of timber 11). In an embodiment, the calculated stiffness (and the correlated strength of the transferred piece of timber 11) can subsequently be used to assign a stress grade to the transferred piece of timber and thereby provide automated stress grading of the pieces of timber 11 being transferred by the rotary timber charger 10.

One skilled in the art will understand that, by determining the deformation of the transferred piece of timber 11 through a comparison of the measured position of the measure surface 11*b* of the transferred piece of timber 11, with and without the force being applied on the contact surface 11*a* of the transferred piece of timber 11 by the load application member 33, over a range of angular positions of the transferred piece of timber 11, the deformation is not influenced by imperfections which can be present at the measure surface 11*b* of the transferred piece of timber 11 (such as, without being limitative, tears, holes, slits or the like), or by a natural curvature of the transferred piece of timber 11. Indeed, the determined deformation is the actual deformation caused by the force being applied on the contact surface 11*a* of the transferred piece of timber 11 by the load application member 33, in comparison to the position measured when no force is being applied on the contact surface 11*a* of the transferred piece of timber 11.

In the embodiment shown, each one of the first surface position measuring assembly 40 and the second surface position measuring assembly 42 includes an optical measuring system (not shown) with a light source (not shown) and a light sensor (not shown), such as, without being limitative, a laser and a camera. Such optical systems are well known in the art and need not be described in more details herein.

In an embodiment, the deformation measuring system 38 also includes a rotary encoder 26 mounted close to the main rotatable shaft 21 and the load application wheel 32. The first surface position measuring assembly 40 and the second surface position measuring assembly 42 are calibrated using the rotary encoder 26, which is used to indicate the angular position of the main rotatable shaft 21, and consequently, the position of the corresponding one of the load application rod(s) 34 of the load application wheel 32 which, in the embodiment shown, interacts with the transferred piece of timber 11 to apply the momentary force on the contact surface 11a thereof.

One skilled in the art will understand that, in alternative embodiments, other systems configured to measure the position of a surface of the piece of timber 11 can also be used. For example and without being limitative, in an embodiment where the actuator used for displacing a component interacting with the transferred piece of timber 11 to apply the force thereon (for example the load application rod(s) 34 or the load application wheel 32 and clamping assembly (not shown)) is a servomotor, or another mechanism using an encoder capable of determining the instant position thereof, the deformation measuring system 38 can be provided by the encoder. Indeed, in such an embodiment, the encoder determines the position of the component interacting with the transferred piece of timber 11 to apply the load thereon and thereby, by extension, the position of a surface of the transferred piece of timber 11, initially (without the force being applied on the transferred piece of timber 11) and upon application of the force on the transferred piece of timber 11 (with the force being applied on the transferred piece of timber 11). Hence, the encoder can measure the position of the surface of the piece of timber 11 at the first and second measurement positions described above.

Moreover, one skilled in the art will understand that, in an alternative embodiment, the first surface position measuring assembly 40 and the second surface position measuring assembly 42 can be embodied in a single assembly with a single optical system where the assembly can be moved or rotated to measure the position of the measure surface 11b of the corresponding transferred piece of timber 11 with and without the force being applied on the contact surface 11a of the transferred piece of timber 11 by the load application member 33. In an alternative embodiment, more than two measuring assemblies can also be used in order to perform measuring of the deformation of the transferred piece of timber 11 over a range of angular positions of the transferred piece of timber 11, as is described in the present description.

In the embodiment shown, the stiffness of the transferred piece of timber 11 is measured by a predetermined load being applied by the load application rods 34 and the resulting deformation being measured and calculated by the deformation measuring system 38. However, one skilled in the art will understand that, in an alternative embodiment, the stiffness of the transferred piece of timber 11 can alternatively be determined by reaching a predetermined deformation of the transferred piece of timber 11 (as determined by the deformation measuring system 38) and measuring the load applied by the corresponding load application member 33, such as the load application rod 34 of the load application wheel 32, in the embodiment shown, in order to reach the predetermined deformation.

Now referring to FIGS. 4a to 4f, an embodiment of a sequence of operation for the stress grading of the pieces of timber 11, during transfer thereof, will be described. In operation, the pieces of timber 11 are successively conveyed transversally on the first carrier assembly 12 towards the rotatable charging assembly 20. When one of the successive pieces of timber 11 reaches the rotatable charging assembly 20, in an embodiment (not shown), the piece of timber 11 is momentarily held against a stopper (not shown) until the rotatable charging assembly 20 is ready to grasp the piece of timber 11.

When the rotatable charging assembly 20 is ready to grasp one of the successive pieces of timber 11, the stopper is retracted and the piece of timber 11 is grasped between the first grasping member 22a and the second grasping member 22b of the timber piece grasping assembly 22 of the rotating transfer wheels 24 (see FIG. 4a).

The rotation of the transfer wheels 24 of the rotatable charging assembly 20 subsequently rotates the transferred piece of timber 11. When the transferred piece of timber 11 has reached a first measurement position, the first surface position measuring assembly 40 measures the position of the measure surface 11b of the transferred piece of timber 11 (See FIG. 4b). In the embodiment shown, the first measurement position corresponds to the position of the piece of timber 11 before the application of the force thereon by a corresponding load application rod 34 of the load application wheel 32.

As the rotation of the transfer wheels 24 of the rotatable charging assembly 20 and the consequent rotation of the transferred piece of timber 11 continue, the load is applied to the contact surface 11a of the transferred piece of timber 11 in order to cause a deformation of the transferred piece of timber 11. In the embodiment shown, the load is applied onto the contact surface 11a of the piece of timber 11 by the load application rod 34 of the load application wheel 32 angularly aligned with the corresponding set of timber piece grasping assembly 22 being brought in the active configuration through actuation of the load application rod 34 by the translation actuator 35 (See FIGS. 4c and 4d). When the transferred piece of timber 11 has reached a second measurement position, the second surface position measuring assembly 42 measures the position of the measure surface 11b of the transferred piece of timber 11 (See FIG. 4d). In the embodiment shown, the second measurement position corresponds to the position of the transferred piece of timber 11 where the deformation is maximal or reaches a predetermined deformation, following the application of the force thereon by the corresponding load application rod 34 of the load application wheel 32. In an embodiment, the deformation is maximal when the load application member 33 is in a maximal extension state.

Figure 4E:
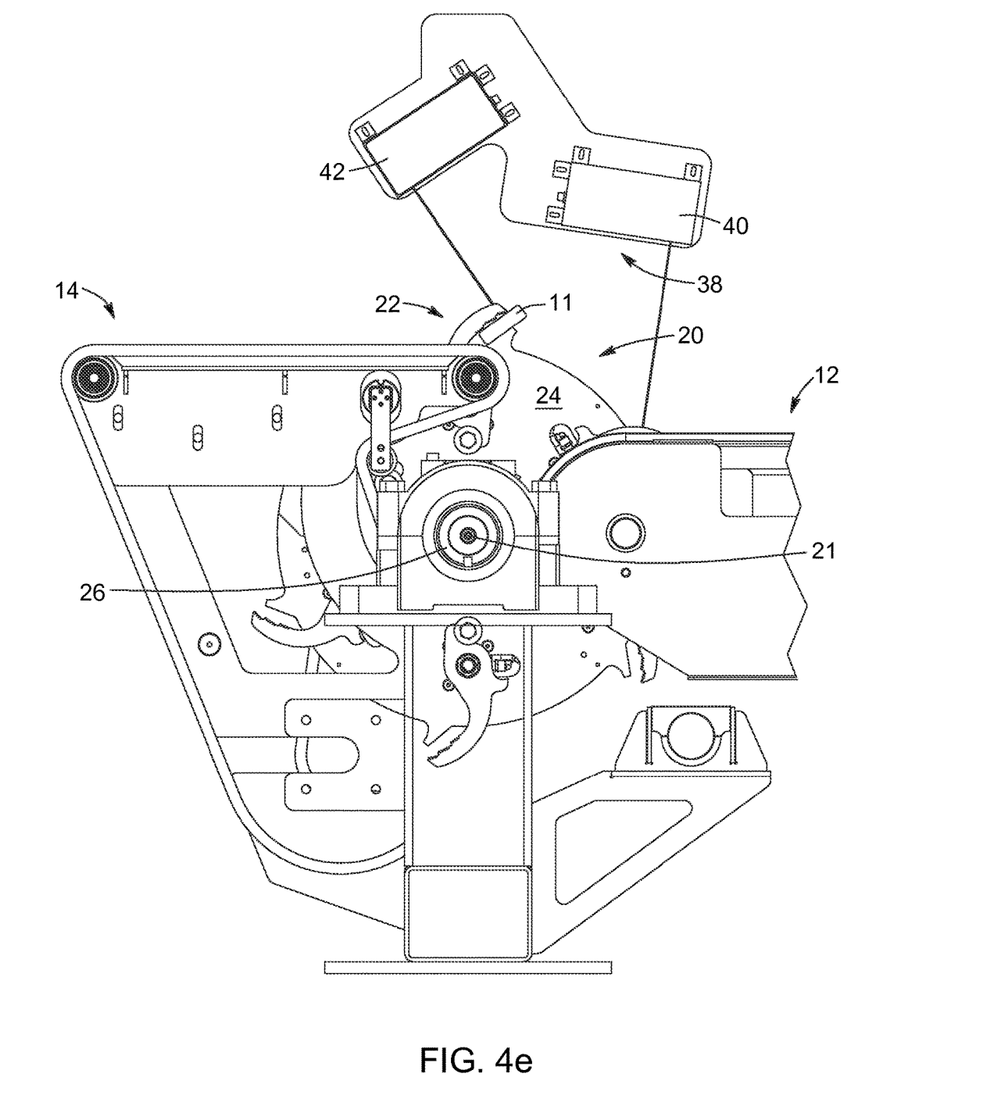
FIG. 4e is a cross-sectional side view of the rotary timber charger including the stiffness measuring mechanism of FIG. 1, with the load application rod disengaged from the piece of timber.

Subsequently, the translation actuator 35 operatively connected to the load application rod 34 of the load application wheel 32, angularly aligned with the corresponding set of timber piece grasping assembly 22 engaging the transferred piece of timber 11, actuates the load application rod 34 rearward to retract the load application rod 34 towards the inactive configuration and therefore remove the force applied on the contact surface 11a of the piece of timber 11, such that the piece of timber 11 returns to its original configuration (See FIG. 4e).

Figure 4F:
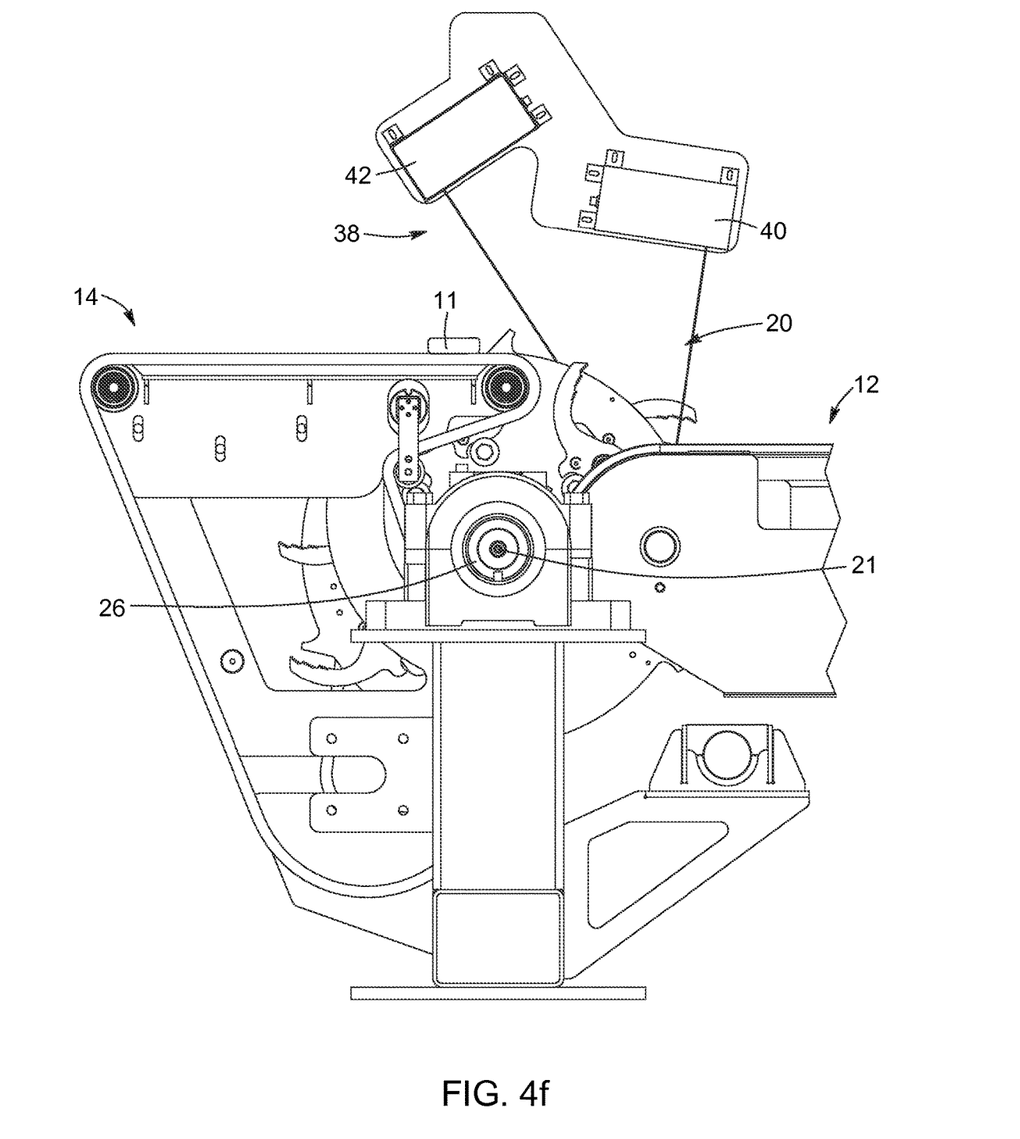
FIG. 4f is a cross-sectional side view of the rotary timber charger including the stiffness measuring mechanism of FIG. 1, showing a piece of timber being released from the rotatable charging assembly.

The piece of timber 11 is subsequently released from the timber piece grasping assembly 22 of the transfer wheels 24 onto the second carrier assembly 14 and is conveyed transversally on the second carrier assembly 14 away from the rotatable charging assembly 20 (see FIG. 4f).

Once again, one skilled in the art will understand that, in an alternative embodiment, the first measurement position can correspond to the position of the transferred piece of timber 11 when the force is applied on the contact surface 11a by the corresponding load application rod 34 of the load application wheel 32 and the second measurement position thereby corresponds to the position of the piece of timber 11 when the force is removed from the contact surface 11a by the corresponding load application rod 34 of the load application wheel 32.

Once again, one skilled in the art will understand that, in an alternative embodiment, not shown, the load can be applied on the surface of the transferred piece of timber 11 through a clamping assembly (not shown) initially engaging the piece of timber 11. In such an embodiment, the clamping assembly would subsequently be displaced in a first direction to apply the force on the transferred piece of timber 11 and cause a deformation of the piece of timber 11. When the force would be applied by the clamping assembly, in an embodiment, the piece of timber would reach the second measurement position where the position of the measure surface 11b of the piece of timber 11 is measured. The clamping assembly would subsequently be displaced in a second direction opposite the first direction to remove the force from the piece of timber 11.

In an embodiment, the above described steps are coordinated by a control system (not shown) based on the data of the rotary encoder 26 which indicate that the transferred piece of timber 11 has reached one of the encoded positions. In other words, the control system operates such that the piece of timber 11 is grasped by the timber piece grasping assembly 22 when the rotary encoder 26 indicates that the timber piece grasping assembly is positioned in the angular position to grasp the piece of timber 11 from the first carrier assembly 12; the first surface position measuring assembly 40 measures the position of the measure surface 11b of the transferred piece of timber 11 when the rotary encoder 26 indicates that the transferred piece of timber has reached a first measured angular position; the translation actuator 35 actuates the corresponding load application rod 34 forward when the rotary encoder 26 indicates that the transferred piece of timber has reached a load application angular position; the second surface position measuring assembly 42 measures the position of the measure surface 11b of the transferred piece of timber 11 when the rotary encoder 26 indicates that the transferred piece of timber has reached a second measured angular position; the translation actuator 35 actuates the corresponding load application rod 34 rearward when the rotary encoder 26 indicates that the transferred piece of timber has reached a load releasing angular position; and the transferred piece of timber 11 is released by the timber piece grasping assembly 22 when the rotary encoder 26 indicates that the timber piece grasping assembly is positioned in the angular position to release the piece of timber 11 onto the second carrier assembly 14.

One skilled in the art will understand that, in an alternative embodiment, other mechanism or method could be used to coordinate the operation of the components in order to perform the above-described steps. In such an embodiment, the rotary encoder can save the angular position of any of the specific components such as, the transfer wheels 24, the load application wheel 32, the load application member 33 and/or a set of timber piece grasping assembly 22, or the like, when one of the steps of the above mentioned method is performed.

One skilled in the art will understand that in an alternative embodiment, the contact surface 11a and the measure surface 11b of the piece of timber 11 could be inverted with respect to the embodiment shown. Moreover, even though in the embodiments shown, the contact surface 11a and the measure surface 11b of the piece of timber 11 are opposed surfaces thereof, one skilled in the art will understand that, in an alternative embodiment, either one of the surfaces of the piece of timber could be used as both the contact surface and the measure surface.

Several alternative embodiments and examples have been described and illustrated herein. The embodiments of the invention described above are intended to be exemplary only. A person skilled in the art would appreciate the features of the individual embodiments, and the possible combinations and variations of the components. A person skilled in the art would further appreciate that any of the embodiments could be provided in any combination with the other embodiments disclosed herein. It is understood that the invention can be embodied in other specific forms without departing from the central characteristics thereof. The present examples and embodiments, therefore, are to be considered in all respects as illustrative and not restrictive, and the invention is not to be limited to the details given herein. Accordingly, while specific embodiments have been illustrated and described, numerous modifications come to mind without significantly departing from the scope of the invention as defined in the appended claims.

The invention claimed is:

1. A rotary timber charger comprising:
   a charging assembly with at least two transfer wheels spaced apart from one another and mounted to a continuously rotating main rotatable shaft, each one of the at least two transfer wheels having at least one timber piece grasping assembly operative to grasp a section of a piece of timber at a grasping position, release the section of the piece of timber at a release position, and retain the section of the piece of timber between the grasping position and the release position, with the piece of timber being continuously moved between the grasping position and the release position; and
   a stiffness measuring mechanism comprising:
      at least one load application wheel positioned between consecutive transfer wheels, each one of the at least one load application wheel comprising at least one load application member configured to momentarily apply a load on the piece of timber retained by a corresponding one of the at least one timber piece grasping assembly of the consecutive ones of the at least two transfer wheels, during rotation of the piece of timber between the grasping position and the release position; and
      a deformation measuring system comprising at least one surface position measuring assembly measuring a deformation of the transferred piece of timber following the application of the load thereon by the at least one load application member, during rotation of the piece of timber between the grasping position and the release position.

2. The rotary timber charger of claim 1, wherein the at least one surface position measuring assembly measures a first position of a measure surface of the piece of timber and a second position of the measure surface of the piece of timber, the second position of the measure surface being angularly spaced-apart from the first position, with the load being applied by the at least one load application member of the at least one load application wheel in at least one of the first position and the second position of the measure surface.

3. The rotary timber charger of claim 2, wherein the at least one surface position measuring assembly of the deformation measuring system includes a first surface position measuring assembly configured to measure one of the position of the measure surface of the piece of timber without the load being applied by the load application member of the at least one load application wheel and the position of the measure surface of the piece of timber with the load being applied by the load application member of the at least one load application wheel and a second surface position measuring assembly configured to measure the other one of the position of the measure surface of the piece of timber without the load being applied by the at least one load application member of the load application wheel and the position of the measure surface of the piece of timber with the load being applied by the load application member of the at least one load application wheel.

4. The rotary timber charger of claim 2, wherein the first position of the measure surface is an angular position thereof without the load being applied by the load application member of the at least one load application wheel.

5. The rotary timber charger of claim 1, wherein the at least one load application wheel is mounted to the main rotatable shaft and rotates simultaneously with the at least two transfer wheels.

6. The rotary timber charger of claim 5, wherein each one of the at least one load application member of the at least one load application wheel includes a load application rod mounted to the load application wheel and a translation actuator operatively connected thereto to translate the load application rod between an inactive configuration wherein a timber piece abutting end of the load application rod is spaced apart from a contact surface of the piece of timber and an active configuration wherein the timber piece abutting end of the load application rod abuts the contact surface of the piece of timber.

7. The rotary timber charger of claim 6, wherein the at least one load application wheel comprises a plurality of load application members and wherein each one of the at least two transfer wheels comprises a plurality of grasping assemblies, the amount of load application members corresponding to the amount of grasping assemblies and each one of the plurality of load application members being angularly aligned with a corresponding one of the plurality of grasping assemblies.

8. The rotary timber charger of claim 1, further comprising a rotary encoder indicating an angular position of the main rotatable shaft and wherein the at least one surface position measuring assembly of the deformation measuring system is calibrated using the rotary encoder.

9. The rotary timber charger of claim 1, wherein each one of the at least one timber piece grasping assembly comprises a first and a second grasping members cooperating to engage opposite surfaces of the piece of timber and the load application member is mounted peripherally to a respective one of the at least one load application wheel and extends substantially tangentially thereto.

* * * * *